United States Patent [19]

Rouchy

[11] 4,139,637
[45] Feb. 13, 1979

[54] QUINONE DERIVATIVES USEFUL AS MEDICAMENTS

[76] Inventor: Maurice Rouchy, Bosseval par Donchery 08, France

[21] Appl. No.: 694,491

[22] Filed: Jun. 9, 1976

Related U.S. Application Data

[63] Continuation of Ser. No. 429,227, Dec. 28, 1973, abandoned.

[30] Foreign Application Priority Data

Dec. 28, 1972 [FR] France ............................... 72.46658

[51] Int. Cl.² ................ A61K 31/175; A61K 31/555; A61K 31/535; A61K 31/445
[52] U.S. Cl. .................................... 424/323; 424/245; 424/248.4; 424/248.5; 424/267
[58] Field of Search ......................................... 424/323

[56] References Cited

PUBLICATIONS

Chemical Abstracts 53: 22479(i), (1959).
Chemical Abstracts 83: 9616(b), (1975).

Primary Examiner—Jerome D. Goldberg
Attorney, Agent, or Firm—Alan H. Levine

[57] ABSTRACT

The present invention relates to new chemical compounds which are useful in particular as medicaments. The compounds are derivatives of a quinone endowed with physiological and particularly vitamin activity and of a substituted hydrazine; they correspond to the following general formulas:

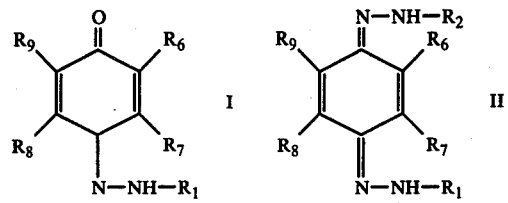

$R_1$ and $R_2$ are identical or different and correspond to the general formula:

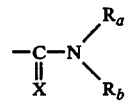

X represents S, Se, O or NH;

$R_a$, $R_b$ are identical or different and are either H, or a branched or unbranched alkyl radical, or the radical —$CH_2NR_4R_5$; in this case $R_4$ and $R_5$ are lower alkyl radicals or else form either a morpholine ring or a methylated piperazine ring, $R_6$ and $R_7$ may be hydrogen, methyl, allyl, phytyl, farnesyl, geranyl, linayl. $R_6$ is different from $R_7$ and one of the two is either hydrogen, methyl or allyl, $R_8$ and $R_9$ are identical or different and are —H, —$CH_3$ or —$OCH_3$, or form the two together a benzene ring.

The compounds in accordance with the invention are endowed with antiviral and vitamin properties and can be administered in therapeutically active doses intravenously, intramuscularly or orally.

4 Claims, No Drawings

QUINONE DERIVATIVES USEFUL AS MEDICAMENTS

This application is a continuation of Application Ser. No. 429,227, filed Dec. 28, 1973, now abandoned.

The present invention relates to new chemical compounds which are useful in particular as medicaments, and more particularly to new antiviral and vitamin agents which can be used both in human medicine and in veterinary medicine.

These compounds are derivatives of a quinone which is endowed with physiological and particularly vitamin activity and of a substituted hydrazine, the reaction taking place with the elimination of water.

The new compounds of the invention correspond to the following general formulas:

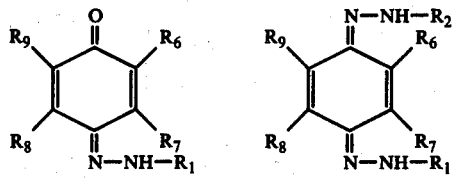

in which formulas:
—$R_1$ and $R_2$ may be identical or different and correspond to the general formula:

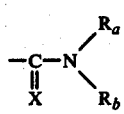

in which:
X represents S, Se; O or else NH,
$R_a$, $R_b$ may be identical or different and represent either H or a branched or unbranched alkyl radical, or the radical —$CH_2NR_4R_5$; in this latter case $R_4$ and $R_5$ may be lower akkyl radicals or else form either a morpholine ring or a methylated piperazine ring.
—$R_6$, $R_7$, $R_8$, $R_9$ are the customary substituents of the basic quinone imparting the physiological and particularly vitamin activity desired.

$R_6$ and $R_7$ may be:
— hydrogen
— the methyl group —$CH_3$
— the allyl group —$CH=CH_2$
— the methallyl group —$CH=CH—CH_3$

- the phytyl group

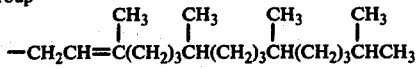

- groups of the formula- —$(CH_2—CH=\overset{CH_3}{\underset{|}{C}}—CH_2)_nH$ in which n is a whole number from 1 to 15

- the linalyl group 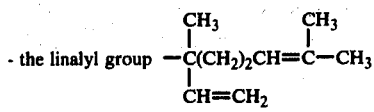

On each molecule $R_6$ is different from $R_7$ and one of the two is either —H, —$CH_3$, or —$CH=CH_2$.

$R_8$ and $R_9$ are identical or different and are either H, —$CH_3$, or —$OCH_3$, or else form together a benzene ring.

In general, the compounds in accordance with the invention are obtained by the action of a substituted hydrazine of the formula $H_2N—NH—R_1$ or $H_2N—NH—R_2$ ($R_1$ and $R_2$ having the meaning indicated above) or of their precursors or by separate action of the two hydrazines on substituted quinones within a solvent, with elimination of water.

The preferred quinones are:
—Menadione and its derivatives having a qualitatively similar vitamin activity, of the formula:

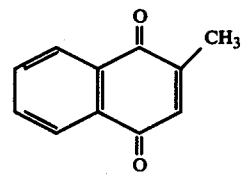

— Tocopheryl quinone and the quinones of qualitatively analogous physiological activity which are obtained either by modification of the phytyl chain — for instance replacement by an allyl, farnesyl, linalyl or geranyl chain — or by removal of substituents from the quinone ring, or else by a combination of the two operations.

— 2-methyl-5,6-dimethoxy quinone

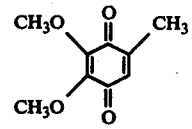

-Phytylmenadiene

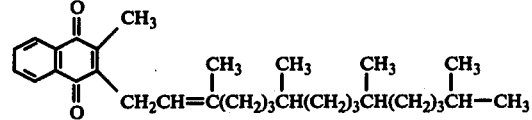

-The ubiquinones

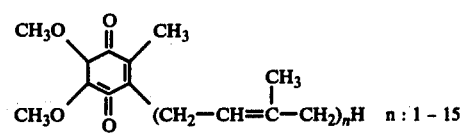 n : 1 - 15

The preferred hydrazines are thiosemicarbazide, selenosemicarbazide, aminoguanidine, aminourea, thiosemicarbazide methylene morpholine, thiosemicarbazide methylene-n-methylpiperazine and allylthiosemicarbazide.

Among the solvenets which can be used in the reaction between the quinone and the hydrazine or hydrazines, mention may be made of the anhydrous or hydrated lower alkanols, the glycol ethers, the disubstituted amides; dimethyl formamide, dimethyl acetamide, N-methyl pyrrolidone, dimethyl sulfoxide, the glycols, water, etc., and mixtures of these solvents in various proportions.

The invention covers not only the compounds of formulas I and II, but also their isomers.

As a matter of fact, these compounds may be present in three forms:

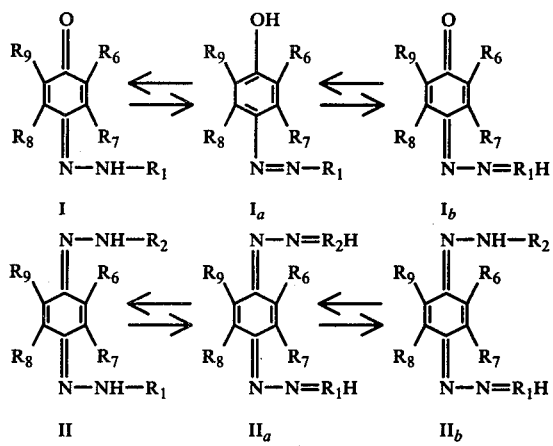

The hydrazones having sulfur and selenium atoms furthermore give the following isomers:

For example, in the case of the derivative resulting from menadione and thiosemicarbazide, the following three forms are present:

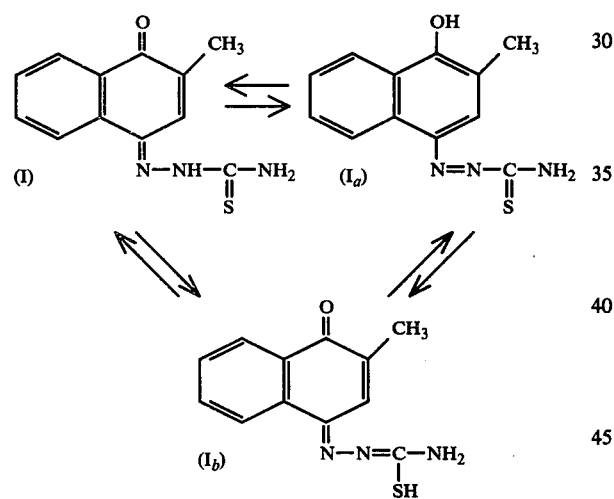

Form I is the most frequent; forms $I_a$ and $I_b$ are present particularly in basic medium.

Therapeutic Activity

The substances forming the object of the present invention are endowed with vitamin properties pertaining to the quinone which has given rise to them. These substances have true antiviral properties, this action being more particularly marked in the case of the monosubstituted hydrazones having a sulfur or selenium atom and in particular the derivatives of thiosemicarbazide.

They may serve, inter alia, for the treatment of Marek's paralysis, Virus K aerosacculitis and other viruses of Barbary duck, virus pneumonia of rabbits, virus pneumonia of calves, pox of fowl and animals, common duck plague, bovine leukoses, myxomatosis, virus enteritis of calves, virus abortion of rabbits, virus hepatitis of mammals and in general numerous types of animal and vegetable virus diseases. The substances may be administered either by intravenous or intramuscular injection, or else orally.

EXAMPLE OF PREPARATION

The following examples are intended to illustrate the invention:

EXAMPLE 1

Into an 11-liter glass round-bottom flask provided with a reflux condenser and an agitating system there are introduced
— 4 liters of pure ethanol
— 2.2 mols of 99.5% crystalline pure menadione, namely about 380 grams.

The mixture is brought to an incipient boil and as soon as everything has dissolved there are then added:
25 ml of pure concentrated 30% HCl, and then immediately:
— 2 mols of crystalline, technically pure thiosemicarbazide which has been previously dissolved in the hot in the smallest possible amount of a mixture of 80% water and 20% DMF (namely about 1 liter).

The addition is effected within a period of time of about four minutes. The liquid is maintained under reflux until reaction commences, as can be noted by an increase in said refluxing and the appearance in the red liquid thus obtained of small, bright yellow crystals which then multiply; termination of the reaction within ten to fifteen minutes following the appearance of these crystals, followed by centrifuging and three washings with absolute ethanol at a temperature of 45° C. makes it possible to obtain a product of the formula:

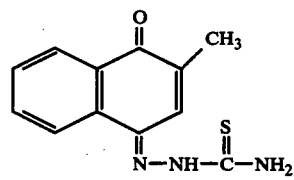

The latter is in the form of scales of the color of old gold. This product, placed on a Maquenne block under a glass slide, melts in 10 to 14 seconds at 275° C., with decomposition.

If the refluxing is continued for one hour and the reaction liquid set aside overnight in the cold, then after centrifuging and washings as described above, there are obtained crystals of a dark reddish brown color corresponding to a mixture of the above product with its isomers whose formulas are:

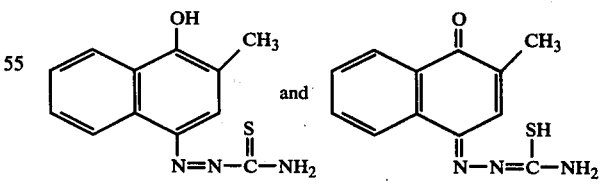

These three substances or their mixture give, in basic medium, an aqueous solution of a red color in high concentration.

EXAMPLE 2

To a boiling alcoholic solution of 2.2 mols of pure menadione under the above conditions there are added two mols of pure aminourea in aqueous solution, one liter of propylene glycol and 20 ml of pure 30% HCl. The mixture is maintained under reflux. After a few moments, crystals start to appear in the medium; the heating is stopped and the product centrifuged one hour after the end of the heating. It is washed in the manner described above three times with 80% hydrated alcohol at a temperature of 35° C. The yield of the operation is 72% of bright yellow crystals of the formula:

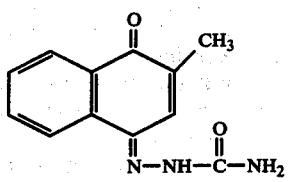

EXAMPLE 3

In the preceding example, the semicarbazide is replaced by two mols of aminoguanidine hydrochloride dissolved in 500 ml of water and the addition of HCl is eliminated. A crystallization of the corresponding aminohydrazone then takes place which, washed three times with 600 ml of a mixture of water, absolute alcohol and sodium bicarbonate in an amount of 20 g/l, gives, after centrifuging and drying, yellow crystals of the formula:

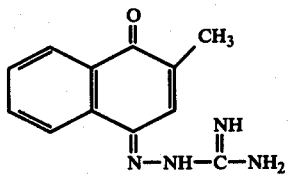

EXAMPLE 4

Into an 11-liter round-bottom flask provided with a reflux and an agitating system there are introduced:
— 2 liters of pure ethanol
— 1 liter of N-methyl pyrrolidone (NMP)
— 1 liter of dimethyl formamide (DMF): and then
— 2 mols of crystalline, pure menadione, namely about 345 grams.

The mixture is brought to boiling with agitation and then there are introduced 3 ml of pure 30% HCl and immediately thereafter 4.8 mols of crystalline thiosemicarbazide previously dissolved in the hot in the smallest possible amount of a mixture of 70% water + 30% DMF. The mixture is maintained under slight reflux for 40 minutes, and then set aside for one hour after addition of 2 liters of pure boiling ethanol.

The brownish yellow crystals which are obtained are centrifuged and washed four times with 4 liters of 70% ethanol at 60° C., and then dried, sheltered from light, at a temperature of about 80° C.

These crystals have the formula:

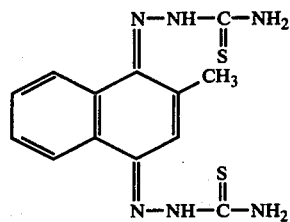

They are soluble in alkalis, giving a dark red color, and give the corresponding basic derivatives on sulfur.

The replacement of the thiosemicarbazide in the above example by aminoguanidine, aminourea or selenosemicarbazide give the corresponding derivatives of the formulas:

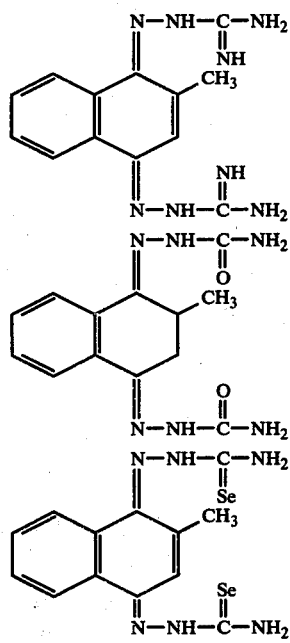

EXAMPLE 5

In a 5-liter round-bottom flask there are introduced:
— 1 liter of N-methyl pyrrolidone (NMP)
— liter of dimethyl formamide (DMF); and then
— 1 mol of the product obtained in Example 1 or one of its position isomers.

The liquid is brought to a temperature of 75° C. until dissolved, whereupon there is added to this reaction liquid; —1.3 mol of thiosemicarbazide dissolved in the hot in the smallest possible amount of a mixture of 30% DMF + 70% water, followed by 15 ml of pure 30% HCl and then after 20 minutes 1 liter of absolute ethanol. The temperature is maintained at 75°/80° C. for 40 minutes; 4 liters of 50% ethanol are added; it is set aside in the cold, centrifuged and washed as in the preceding examples. The same product is obtained as in the preceding example.

EXAMPLE 6

If 1.2 mol of aminourea is added to the solution of Example 5, one obtains by the same procedure the corresponding asymmetric bis-aminohydrazone of the formula:

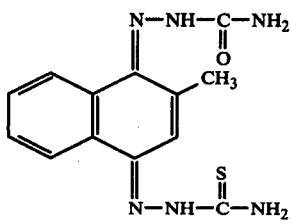

Likewise, if the aminourea is replaced by aminoguanidine, there is obtained a compound of the formula:

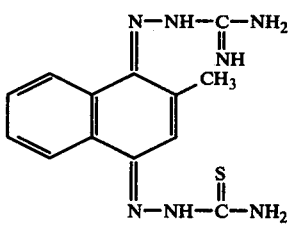

EXAMPLE 7

In Example 1 the menadione is replaced by 2-methyl-5,6-dimethoxy quinone. Yellow crystals are obtained of the formula:

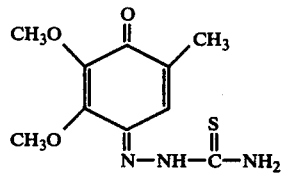

By replacing the menadione by this quinone in the same manner as in the previous examples, one successively obtains the corresponding hydrazones.

In general, the products in accordance with the invention are insoluble or practically insoluble in water, the lower alkanols and the glycols; they are soluble in DMF, DMSO and N-methyl pyrrolidone, giving dark red solutions, and are soluble in aqueous solutions of mineral bases (soda, potash, etc.) and organic bases (choline, aminoethanol, etc.).

The compounds of the invention have been tried out in the treatment of the diseases indicated in the following examples:

EXAMPLE A:

Marek's paralysis

32 Leghorn hens, 9 weeks of age, contaminated and having initial symptoms of Marek's paralysis, are divided into two lots — one lot of 72 controls and one lot of 20 treatment subjects. The latter receive an intramuscular injection of 45 mg/kg of the product of Example 1, previously dissolved in dimethyl sulfoxide for 6 days, and then 40 mg/kg per day in drinking water for 8 days.

One month after the start of the treatment, the results are as follows:

Controls: 1 survivor paralyzed in course of death
Treated subjects: 16 survivors, 14 of which present no symptom and 2 present only slight symptoms of paralysis. The 14 healthy survivors have resumed their growth in normal manner.

EXAMPLE B

Virus K aerosacculitis of Barbary duck

A lot of 1500 Barbary ducklings 18 days of age, presenting the symptoms of this disease, is divided into two lots of 750 subjects each. A control lot and a lot subjected to treatment in a dose of 45 mg/kg of active principle of Example 1 per kg of live weight on the first three days and 35 mg/kg on the next 5 days.

The results after 15 days are as follows:
Lot treated: mortality: 2
Lot not treated: mortality: 148

Furthermore, the subjects treated are of uniform weight and have resumed a normal growth; on the other hand, the survivors of the untreated lot show considerable differences in weight, and among them, some ducklings limp, no longer grow in size and no longer grow feathers.

EXAMPLE C:

Virus pneumonia of rabbits.

In a hutch where this disease prevails, 3 lots are formed of 20 rabbits each.

The first lot receives the product of Example 1 in a dose of 35 mg/kg, dissolved in dimethyl sulfoxide.

The second lot receives a combination of tetracycline and sulfamide in adequate doses intramuscularly.

The third lot receives a combination of spiramycin-dihydrostreptomycin in suitable doses.

Results after two weeks:
1st lot: 18 survivors gaining weight and eating normally.
2nd lot: 2 survivors continuing to lose weight.
3rd lot: 3 survivors continuing to lose weight.

Similar results were obtained with the other compounds in accordance with the invention and particularly those mentioned in the other examples.

The compound of Example 1 has an antitumor activity and permits the resorption of various organic tumors.

The compound of Example 4 has proven to be of similar activity in virus enterites of rabbits and calves.

The compound of Example 7 has an activity of the same order and exerts a synergistic action with the preceding compounds.

The molecules of these compounds retain qualitatively the vitamin activity of the base quinone, as proven by the antihemorrhagic action of the derivatives of vitamin $K_3$.

GALENIC FORMS

The compounds in accordance with the invention can be presented in the customary pharmaceutical forms employing the conventional methods of preparation — in the form of solutions, depending on the solubility of the products, suspensions, powders or suppositories, and other forms.

The active therapeutic doses, by mouth or otherwise, are between 3 and 150 mg/kg, depending upon the viruses and the animals; higher doses are tolerated by small animals.

We claim:

1. A method of treating a viral disease in an animal which comprises administering to the afflicted animal an antiviral dose of the following compound or its isomer:

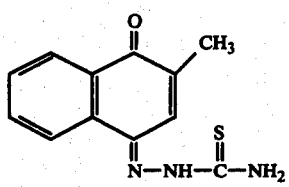

2. A method of treating Marek's paralysis in an animal which comprises administering to the afflicted animal an amount sufficient to relieve Marek's paralysis of the following compound or its isomer:

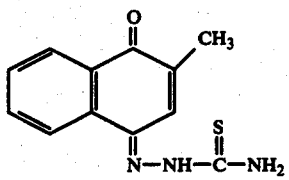

3. A method of treating Virus K aerosacculitis of Barbary Duck which comprises administering to said afflicted animal an amount effective to relieve Virus K aerosacculitis of the following compound or its isomer:

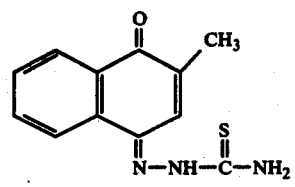

4. A method of treating virus pneumonia of rabbits which comprises administering to said afflicted animals an amount sufficient to relieve virus pneumonia of rabbits of the following compound or its isomer:

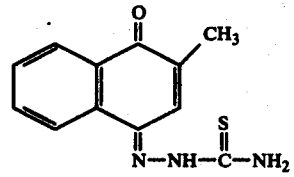

* * * * *